US012743722B2

(12) United States Patent
Nielson

(10) Patent No.: US 12,743,722 B2
(45) Date of Patent: Sep. 22, 2026

(54) METHODS FOR USE OF 3D BODY SCANS FOR COMPARATIVE VISUALIZATION AND EVALUATION OF GARMENT FIT OR BODY CHANGES OVER TIME

(71) Applicant: Swipe Fashion Incorporation, Fernie (CA)

(72) Inventor: Kevin W. Nielson, Regina (CA)

(73) Assignee: Swipe Fashion Incorporation, Fernie (CA)

( * ) Notice: Subject to any disclaimer, the term of this patent is extended or adjusted under 35 U.S.C. 154(b) by 0 days.

(21) Appl. No.: 19/395,495

(22) Filed: Nov. 20, 2025

(65) Prior Publication Data

US 2026/0148289 A1 May 28, 2026

Related U.S. Application Data

(60) Provisional application No. 63/724,691, filed on Nov. 25, 2024.

(51) Int. Cl.
*G06Q 30/0601* (2023.01)
*A61B 5/00* (2006.01)
*A61B 5/107* (2006.01)

(52) U.S. Cl.
CPC ..... *G06Q 30/06432* (2025.08); *A61B 5/0064* (2013.01); *A61B 5/1077* (2013.01); *A61B 5/1079* (2013.01); *A61B 2503/12* (2013.01)

(58) Field of Classification Search
CPC ............ G06Q 30/06432; A61B 5/0064; A61B 5/1077; A61B 5/1079

(Continued)

(56) References Cited

U.S. PATENT DOCUMENTS 2,056,740 A 10/1936 Rosenfeld
2,181,325 A 11/1939 Greneker
(Continued)

FOREIGN PATENT DOCUMENTS

CN 203341056 12/2013
CN 203482294 3/2014
(Continued)

OTHER PUBLICATIONS

Magic Mirror, Virtual Dressing Kiosk, found on the website www.magicmirror.me/Apps/3D-Virtual-Dressing (2018) (Year: 2018).*

*Primary Examiner* — Ashley D Preston
(74) *Attorney, Agent, or Firm* — Kyle R Satterthwaite; Ryan W Dupuis; Ade & Company Inc

(57) ABSTRACT

A method of garment fit assessment in the context of online shopping stores a 3D body scan of a fashion influencer who has been visually documented online wearing a purchasable garment, receiving a 3D body scan of a shopper, and, from the 3D body scans of the influencer and shopper, creating a comparative digital 3D body model that visually overlays the two 3D body scans to reveal differences in body size and shape between the shopper and influencer. From an online viewing of the comparative model, the shopper can visually gauge a body similarity between the shopper and influencer to gauge how the garment, as seen worn on the influencer, will fit the shopper. In other embodiment, instead of comparative evaluation against an influencer's body scan, the system overlays multiple body scans of a singular user at different points in time, for visualization of the individual's body changes over time.

20 Claims, 6 Drawing Sheets

(58) Field of Classification Search
USPC ................................................ 705/26.1–27.2
See application file for complete search history.

(56) References Cited

U.S. PATENT DOCUMENTS

| | | | |
|---|---|---|---|
| 2,445,458 | A | 7/1948 | Otta |
| 2,529,125 | A | 11/1950 | Barbera |
| 2,720,347 | A | 10/1955 | Jackson |
| 2,740,565 | A | 4/1956 | Wells |
| 3,382,504 | A | 5/1968 | Tamayo |
| 3,710,994 | A | 1/1973 | Cherry et al. |
| 4,828,528 | A | 5/1989 | Chatkis |
| 5,340,350 | A | 8/1994 | Fink et al. |
| 5,419,729 | A | 5/1995 | Gross |
| 6,310,627 | B1 | 10/2001 | Sakaguchi |
| 6,413,142 | B1 | 7/2002 | Weastler |
| 6,805,606 | B1 | 10/2004 | Kellum |
| 9,554,096 | B1 | 1/2017 | Eakins |
| 9,696,130 | B1 | 7/2017 | Eakins |
| 9,984,588 | B1 | 5/2018 | Barker |
| 10,460,525 | B1 | 10/2019 | Buuck et al. |
| 11,559,097 | B2 * | 1/2023 | Modi ...................... G06T 19/00 |
| 11,596,836 | B2 | 3/2023 | Kim et al. |
| 2004/0036841 | A1 | 2/2004 | Dbjay |
| 2005/0051581 | A1 | 3/2005 | Nan |
| 2005/0154487 | A1 | 7/2005 | Wang |
| 2007/0298185 | A1 | 12/2007 | Nan |
| 2008/0262944 | A1 | 10/2008 | Wu |
| 2010/0320240 | A1 | 12/2010 | Sadaoka |
| 2012/0284148 | A1 | 11/2012 | Volchek |
| 2013/0238285 | A1 | 9/2013 | Volchek |
| 2015/0112648 | A1 | 4/2015 | Abu Al Rubb |
| 2015/0287242 | A1 | 10/2015 | Kim et al. |
| 2016/0042667 | A1 | 2/2016 | Kusafuka |
| 2016/0275600 | A1 * | 9/2016 | Adeyoola .......... G06Q 30/0643 |
| 2017/0228911 | A1 | 8/2017 | Zylberberg et al. |
| 2019/0080390 | A1 | 3/2019 | Chervinski |
| 2022/0197963 | A1 | 6/2022 | Kincl |
| 2022/0309567 | A1 * | 9/2022 | Han ..................... G06V 40/103 |
| 2023/0290030 | A1 | 9/2023 | Muhlenfeld |
| 2024/0177388 | A1 * | 5/2024 | Johl ....................... G06N 3/006 |

FOREIGN PATENT DOCUMENTS

| | | |
|---|---|---|
| CN | 204065655 | 12/2014 |
| CN | 105301887 | 2/2016 |
| DE | 102007052300 | 5/2009 |
| KR | 20180060160 | 6/2018 |
| KR | 102437199 | 8/2022 |
| WO | 2011141646 | 11/2011 |

* cited by examiner

COMPARATIVE BODY
SCAN VISUALIZATION
(shown to shopper, e.g. during browsing and/or order placement/checkout)

| | A | B | A - B |
|---|---|---|---|
| **Height** | 172 cm | 168 cm | + 4 cm |
| **Shoulders** | 32 cm | 29 cm | + 3 cm |
| **Chest** | 82 cm | 79 cm | + 3 cm |
| **Waist** | 68 cm | 65 cm | + 3 cm |
| **Hips** | 86 cm | 81 cm | + 5 cm |
| **Thigh** | 49 cm | 44 cm | + 5 cm |
| **Calf** | 36 cm | 34 cm | + 2 cm |
| **Inseam** | 60 cm | 58 cm | + 2 cm |

METHODS FOR USE OF 3D BODY SCANS FOR COMPARATIVE VISUALIZATION AND EVALUATION OF GARMENT FIT OR BODY CHANGES OVER TIME

CROSS-REFERENCE TO RELATED APPLICATIONS

This application claims benefit under 35 U.S.C. 119(e) of Provisional Patent Application No. 63/724,691, filed Nov. 25, 2024, the entirety of which is incorporated herein by reference.

FIELD OF THE INVENTION

The present invention relates generally to online shopping, and more particularly to computer implemented systems and methods enabling online shoppers to better gauge the anticipated fit of purchasable garments based on comparative fit of those garments seen in posted online content by other wearers of those garments.

BACKGROUND

Shopping for garments online as an alternative conventional brick and mortar retail has become more and more commonplace. Online shopping is very convenient since a user can access from the comfort of their computer or mobile device a very large selection of garment items that is not limited by available on-hand inventory at retail locations of proximity to the buyer, and in many cases makes it possible to shop competitively for the best possible price among different online sellers.

One of the main challenges of online shopping for garments is that the shopper cannot try on the actual item, and thus risks purchasing a garment that may not fit, or that even if a good match from a fitting perspective, for one reason or another doesn't aesthetically look as good as anticipated. Compounding this challenge are the facts that human bodies come in all shapes and sizes, and garments come in many styles and sizes, and both are subject to continuous or periodic, and sometimes rapid, change.

Given all these considerations, selection of the appropriate garment size to purchase and assessment of anticipated garment fit for a particular shopper's body at the selected size is challenging, often frustrating, and frequently results in an unsatisfactory outcome, often necessitating return of the purchased garment for exchange or refund, denoting a hassle for both the buyer and seller, which is not always a viable option depending on seller return/refund policies and the cost of return shipping, the responsibility of which sometimes resides with the seller and other times with the buyer, depending on said policies. In the case of international orders, not only can the cost of return shipping be significant, but cross-border transactions also have extra considerations, such as preparation of appropriate customs documentation, and sunk costs or refund hassles of taxes/duties paid on the original shipment.

Prior efforts to address the challenge of size/fit assessment in the online garment shopping experience have been proposed in prior patent literature.

Published US Patent Application 2022/0197963 by Kince Inc. discloses an online garment system designed to match shoppers with fashion influencers based on similarity of body type, so that the shoppers can use the photographic/videographic imagery of fashion influencers modeling purchasable garments to assess the suitability of the garment's fit for the shopper's body type. A compilation of body measurements are used to generate searchable code for each influencer against which the shopper's body measurements can be searched to find comparable body matches.

Korean Patent KR102437199 appears to disclose something similar, but as best Applicant can tell from readily available machine translation, makes only general reference to "body type information" inputted by the user, and some sort of AI model that selects a matching influencer based on this body type information and user questionnaire information.

Published US Patent Application 2019/0080390 by Tiger Fox Marketing Ltd. discloses a workflow in which User A registers, enters an initial body type from available categories and their specific body measurements, which measurements are used to update the body type. User A then uploads photos and videos wearing garment items and associated tags, by which User A is linked to garment items in a database. User B similar registers and enters their body measurements to get assigned a body type. When User B searches for garment items, search results are given as photographs/videos of other users of matching/similar body type wearing those garment items.

In each of these examples, it remains somewhat unclear the degree of accuracy achievable in the attempted assessment of a garment's true fit on a shopper's body based on the type of body categorization, body measurement and body matching employed tactics employed in these prior solutions, especially given the large variability between precise body measurements of two users that could be generally categorized as sharing a similar body type.

Accordingly, there remains room for notable improvement in similarity matching and comparative analysis of body shape and size to enable an online shopper to achieve better assessment of anticipated garment fit.

SUMMARY OF THE INVENTION

According to a first aspect of the invention, there is provided a computer-implemented method of enabling garment fit assessment by a garment shopper, said method comprising:

(a) storing in non-transitory computer readable memory a 3D body scan of a garment wearer who has been visually documented wearing one or more purchasable garments, visual documentation of which is available for online viewing by said garment shopper using an electronic device connected to a communications network;

(b) receiving a 3D body scan of said garment shopper;

(c) from said 3D body scans of the garment wearer and the garment shopper, creating a comparative digital 3D body model that embodies visually overlaid representations of at least parts of the 3D body scans of the garment shopper and the garment wearer, in visually distinctive relation to one another to reveal differences in body size and shape between the garment shopper and the garment wearer; and (d) enabling remote viewing of said comparative digital 3D body model by said garment shopper over said communications network, from which remote viewing said garment shopper can visually gauge a body similarity between said garment shopper and said garment wearer, which in combination with viewing by the shopper of said visual documentation of the garment wearer and the one or more purchasable garments, enables informed judgement by said garment shopper as to how well any of said one or more purchasable garments would fit said garment shopper.

According to a second aspect of the invention, there is provided a computer-implemented method for visualization of a change in body shape of a user over time, said method comprising:

(a) receiving and storing in non-transitory computer readable memory an initial 3D body scan of the user reflective of the body shape of said user at a first point in time;

(b) after passage of time, receiving and storing in non-transitory computer readable memory an updated 3D body scan of the user reflective of an updated body shape of said user at second point in time;

(c) from said initial and updated 3D body scans of the user, creating a comparative digital 3D body model that embodies visually overlaid representations of at least parts of the initial and updated 3D body scans of the user, in visually distinctive relation to one another to reveal one or more changes in body shape that have occurred between said first and second points in time; and (d) enabling display said comparative digital 3D body model as visualized feedback on said one or more changes in body shape.

The method may include, based on the initial and updated 3D body scans of the user, calculation of one or more body differential values each corresponding to a measurement difference, in a respective body measurement, between the initial and updated 3D body scans of the user.

Step (d) may include enabling viewable display of at least one of said one or more body differential values to the user in a same user interface in which said comparative digital 3D body model is viewable, thereby providing quantifiable measure of the change in body shape in combination with visualization of change in body shape.

According to a third aspect of the invention, there is provided a computer-implemented method of enabling garment fit assessment by a garment shopper, said method comprising:

(a) storing in non-transitory computer readable memory both:

a 3D body scan of a garment wearer who has been visually documented wearing one or more purchasable garments, visual documentation of which is available for online viewing by said garment shopper using an electronic device connected to a communications network; and for at least one of said purchasable garments, a 3D body-analogue scan of a variably inflatable human body analogue at an inflated size thereof corresponding to a maximally stretched state of said one of said purchasable garments;

(b) receiving a 3D body scan of said garment shopper;

(c) performing computer-automated comparative analysis of said 3D body scan of said garment shopper against both said 3D body scan of said garment wearer and said 3D body-analogue scan; and (d) for evaluative assessment by the garment shopper of a fit of the garment on said garment shopper, enabling viewing by the garment shopper of a comparative visualizer that comprises:

(i) at least one of:

a 3D visualization of wearer body shape, as derived from the 3D body scan of the garment wearer; and a 3D visualization of the garment as would appear in a worn state thereof on the garment wearer, as derived from the 3D body scan of the garment wearer;

(ii) at least one of:

a 3D visualization of shopper body shape, as derived from the 3D body scan of the garment shopper;

a 3D visualization of the garment as would appear in a worn state thereof on the garment shopper, as derived from the 3D body scan of the garment shopper; and (iii) one or more indicators of computer evaluated fit of the garment, as derived from said computer-automated comparative analysis.

The comparative visualizer may further comprise a 3D visualization of the garment as would appear in the maximally stretched state thereof.

Preferably said evaluative assessment by the garment shopper of the fit of the garment on said garment shopper comprises:

calculation of one or more body differential values each corresponding to a measurement difference, in a respective body measurement, between the 3D body scan of the garment shopper and the 3D body scan of the garment wearer; and calculation of one or more body stretch-fit deviation values each corresponding to a difference between a body measurement, at a respective body part, of the 3D body scan of the garment shopper and a garment measurement at a corresponding part of said one of the garments in the maximally stretched-state thereof;

wherein the one or more indicators of computer evaluated fit of the garment are comprised of, or derived from, at least a subset of said differential and deviation values.

The comparative visualizer may comprise one or more visual overlays each showing an overlay of any two or more the 3D visualizations.

According to a fourth aspect of the invention, there is provided a computer-implemented method of enabling garment fit assessment by a garment shopper, said method comprising:

(a) storing in non-transitory computer readable memory a reference model of a garment of given size designation in a maximally stretched state of said garment;

(b) receiving a 3D body scan of said garment shopper;

(c) from said reference model and said 3D body scan of the garment wearer, creating comparative stretch-fit digital 3D body model that embodies overlaid visual representations of the reference model and the 3D body scan of the garment shopper, in visually distinctive relation to one another to reveal differences between the body size and shape of the garment shopper and the maximally stretched state of said one of said purchasable garments; and (d) enabling viewing of said stretch-fit digital 3D body model by said garment shopper over said communications network, from which viewing said garment shopper can visually gauge an anticipated fit of the garment on said garment shopper taking into account a maximum stretchability of said garment.

The method preferably includes, based on the reference model and the 3D body scan of the garment shopper, calculation of one or more body-garment stretch-fit deviation values each corresponding to a difference between a body measurement, at a respective body part, of the 3D body scan of the garment shopper and a stretched garment measurement at a corresponding part of said one of the garments in the maximally stretched-state thereof.

The method preferably includes enabling viewable display of at least one of said one or more body-garment stretch-fit deviation values to the garment shopper in a same user interface in which viewing access to said comparative stretch-fit digital 3D body model is provided, thereby providing quantifiable measure of a garment looseness or tightness at one or more body parts where said body measurement differ from the stretched garment measurement.

According to a fifth aspect of the invention, there is provided a computer-implemented method of enabling garment fit assessment by a garment shopper, said method comprising:

(a) storing in non-transitory computer readable memory a reference model of a garment of given size designation in a maximally stretched state of said garment;
(b) receiving a 3D body scan of said garment shopper;
(c) based on the reference model and the 3D body scan of the garment shopper, calculation of one or more body-garment stretch-fit deviation values each corresponding to a difference between a body measurement, at a respective body part, of the 3D body scan of the garment shopper and a stretched garment measurement at a corresponding part of said one of the garments in the maximally stretched-state thereof;
(d) enabling viewable display of at least one of said one or more body-garment stretch-fit deviation values to the garment shopper, thereby providing quantifiable measure of a garment looseness or tightness at one or more body parts where said body measurement differ from the stretched garment measurement.

Said reference model may be a 3D body-analogue scan captured of a dynamically shape and size adjustable human body analogue on which the garment was stretched to its maximally stretched state to derive said reference model.

According to further aspects of the invention, there are provided systems for respectively executing each of the forgoing methods, each comprising one or more processors coupled to one or more non-transitory computer readable media in which there are stored computer readable statements and instructions executable by said one or more processors so as to, when executed, perform at least step (a) through (d) of the respective method.

According to another aspect of the invention, there is provided one or more non-transitory computer readable media in which there are stored computer readable statements and instructions executable by one or more processors so as to, when executed, perform at least step (a) through (d) of any one or more of the preceding methods.

BRIEF DESCRIPTION OF THE DRAWINGS

Preferred embodiments of the invention will now be described in conjunction with the accompanying drawings in which.

DETAILED DESCRIPTION

Figure 1:
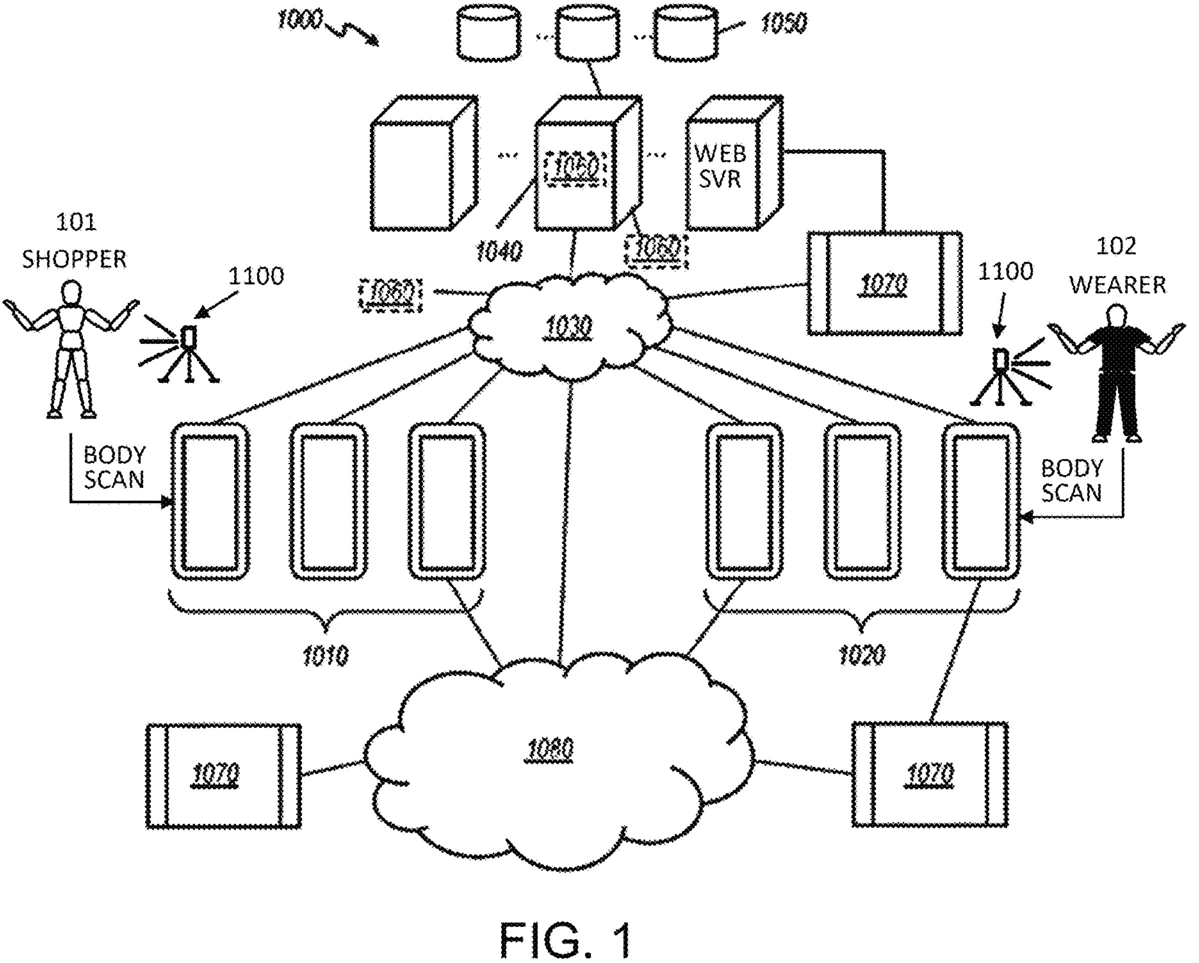
FIG. 1 is a block diagram of an inventive system for enabling accurate fit assessment of garments in an online shopping context through body-based matchup of online shoppers and fashion influencers and visualization of body similarity therebetween using overlaid 3D body scans.
Figure 2:
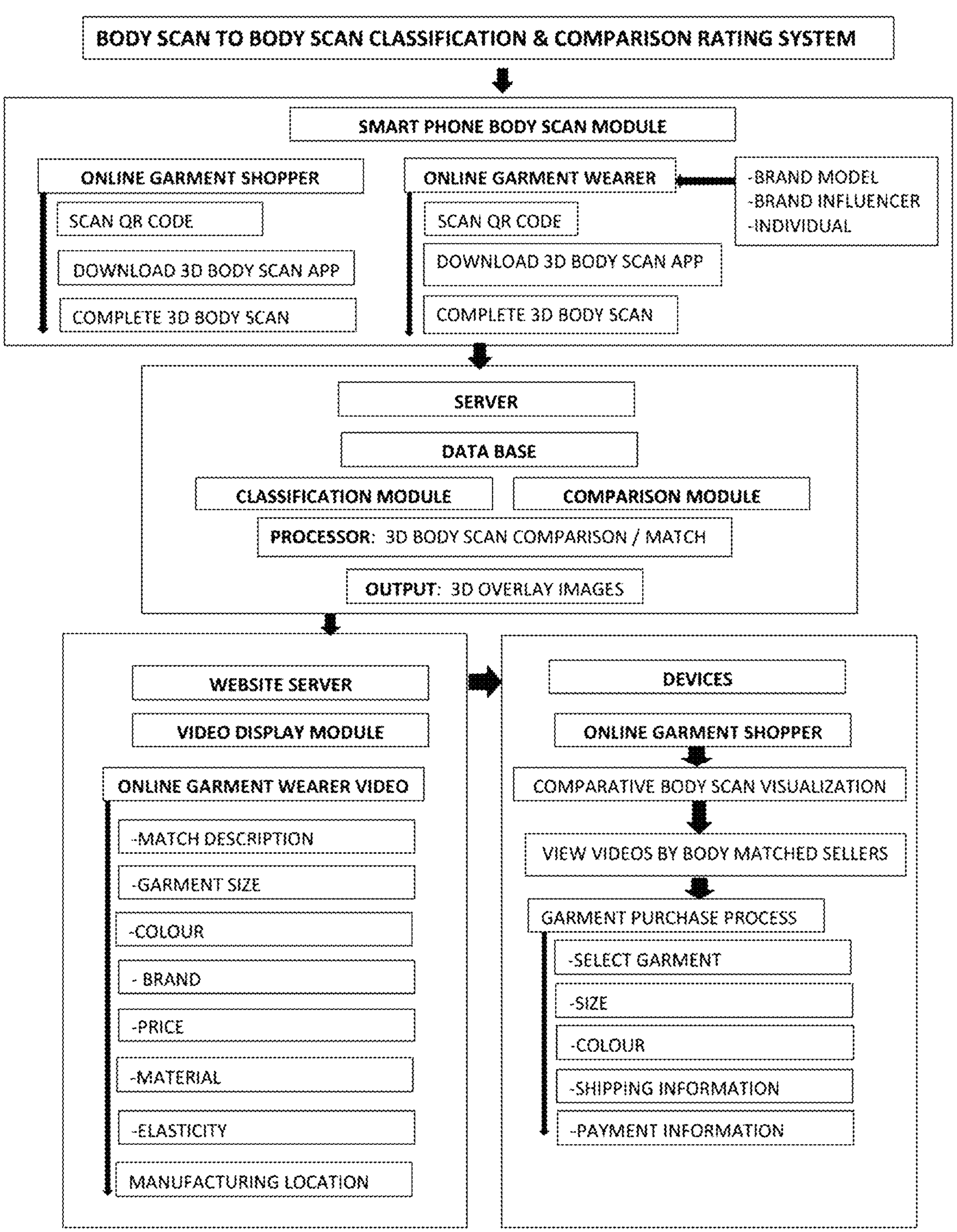
FIG. 2 is a combined block diagram and flowchart schematic illustrating workflow steps performed by and with the system of FIG. 1 in inventive methodologies of the present invention.

Turning now to FIG. 1, illustrated is one embodiment of an exemplary system 1000 constructed and implemented in accordance with the disclosed principles of the present invention. Generally speaking, there are two types of users of the system: garment shoppers and garment wearers, among which garment shoppers are persons shopping online for one or more garments to purchase, and garment wearers are persons who have each already worn one or more garments that are available for online purchase, and which one or more adorned instances of those one or more garments by that garment wearer were documented photographically and/or videographically, and which photographic and/or videographic documentation is posted online and therefore viewable remotely by the garment shoppers. Such viewing enables a visual estimation by a garment shopper of how the one or more garments being shopped for might fit on the shopper based on a similarity of the shopper's body size and shape to those of a one or more of the garment wearers to whom the garment shopper is matched in body similarity. In some embodiments, it is envisioned that the garment wearers will typically be known online personalities, such as fashion influencers or content creators, for example having sponsorships with garment brands or retailers whose garments are the subject garments photographically/videographically modeled by such persons, though this need not necessarily be the case in all embodiments or instances, as paid fashion models of little or no public recognizability could instead serve the role of some or all of the garment wearers, and prior buyers of the garments available for sale could voluntarily upload photographic/videographic content of the them wearing such garments, for body matching of such prior buyers to new shoppers for the same garment assessment purpose based on body similarity.

Illustrated in FIG. 1 is a plurality of garment shopper devices 1010 possessed by a respective plurality of garment shoppers 101 (schematically represented in the singular) and each having thereon one or more software executable applications thereon for the purpose of performing any or all tasks attributed herein to any garment shopper or their garment shopper device. Although the collection of garment shopper devices 1010 are illustrated in this embodiment as smartphones, it is understood that one or more of the devices 1010 may also be implemented as tablets, desktop computers, or any other type of computing device capable of executing software applications as disclosed herein and to interconnect to one or more communications networks. As discussed in detail herein, the shopper devices 1010 are operated by corresponding garment shoppers in the manner and for the purposes as disclosed herein. It will be appreciated that software applications are typically embodied as executable statements and instructions stored in one or more non-transitory computer readable media that are connected to one or more processors of the device for execution by those one or more processors to perform the tasks, steps, processes and algorithms described herein.

Also illustrated in FIG. 1 is a plurality of garment wearer devices 1020 possessed by a respective plurality of garment shoppers 102 (schematically represented in the singular). As with the shopper devices 1010, the garment wearer devices 1020 each have thereon one or more executable software applications for the purpose of performing any or all tasks attributed herein to any garment wearer or their garment wearer device. Also, as with the shopper devices 1010, the garment wearer devices 1020 may also be implemented as smartphones, tablets, desktop computers, or any other type of computing device capable of executing software applications as disclosed herein and of interconnecting to one or more communications networks.

Also illustrated in FIG. 1 is a system communications network 1030. The network 1030 may be implemented as a dedicated private communications network, or may comprise a public communications network. In addition, the network 1030 over which the disclosed system 1000 is implemented may be any type of communications network, such as a data packet network, a packet-switched network, a part of the publicly-accessed Internet, or any other type of computer or communications network whether wired, wireless or both. As illustrated, the garment shopper devices 1010 and the garment wearer devices 1020 are connected to and communicate across the system network 1030 using any type of communications protocol either now existing or later developed, and such communication is facilitated via the corresponding plurality of applications implemented in accordance with the disclosed principles.

Also connected to the system network 1030 and comprising a part of the disclosed system 1000 is a computer server 1040. As illustrated, the server 1040 may be implemented as a single server or may be implemented as a collection of multiple servers, as needed. Each such server 1040 comprises both hardware, firmware and software, as well as a communications interface, for communicating and implementing the disclosed principles across the system network 1030 and with one or more of the garment shopper devices 1010 and garment wearer devices 1020. In communication with the one or more servers 1040 are one or more storage databases 1050. Such databases 1050 are comprised of both hardware, firmware and software, and configured for creating, storing and accessing data files and folders, including the garment shopper and garment wearer profiles disclosed herein.

Within the system hardware, such as one or more of the servers 1040 or in one or more computing devices, or other hardware in communication with the servers and/or the databases 1050 and network 1030, are one or more computer processors 1060. Such processor(s) 1060 comprises hardware for executing software and/or firmware for implementing the principles disclosed herein. As shown, such processor(s) 1060 may be included within a server 1040, of maybe be comprised in a separate computing component in communication with the server 1040 either directly through a wired or wireless interface, or in communication via the system network 1030. Of course, other architectures for providing the one or more processors 1060 may be implemented with a system as disclosed herein. Moreover, the processor(s) 1060 is a specialized computing component having hardware, firmware and software, as required, for implementing a system 1000 or related service in accordance with the principles disclosed herein. Included among these implemented principles is the facilitating of communication with the software applications executed on the garment shopper and garment wearer devices 1010, 1020 for not only creating and causing the storage of shopper and wearer profiles in the databases 1050, but also for providing the matching of wearers to shoppers, and visualization, in some instances combined with quantification, of body similarity of each shopper to the wearer(s) matched thereto, as described in detail herein below.

Such matching of garment wearers to garment shoppers by capturing 3D body scans of both user types by the processor(s) and interconnected hardware and software of the disclosed system 1000, and then comparing those 3D body scans among shoppers and wearers to ensure a quality fit assessment for garment items, provides a novel solution to a problem that arises in computer-based (e.g., online) environments. Specifically, when a garment shopper browses and shops for garments online, the computer-based environment of online shopping creates the problem of how the shopper can be certain that a garment item fits their particular body size/measurements. In the traditional brick-and-motor shopping environment, the shopper would simply try on the garment to ensure a proper fit. But such trying on is not possible in the online shopping realm. The solution of simply ordering garments for trying on at home and then returning those that do not fit is not a solution to this computer-based conundrum since not only is such shipping and returning of items costly, time-consuming and tedious, but such a solution simply converts the online shopping experience to an in-person try-on experience. Even an online shopper trying to "eyeball" a garment wearer or model online in an effort to determine if a particular garment would fit them based on how it fits the wearer does not alone provide a viable solution to the computer-based problem since doing so does not provide any certainty to the results of such a guessed fit. Instead, the disclosed principles provide a novel computer-based solution to a problem that is necessarily rooted in the computing environment of online shopping by searching for and matching garment wearers that have been mathematically determined, through computer-automated analysis of 3D body scan data, to have the same (or very similar) body measurements as the garment shopper shopping online.

Also illustrated in FIG. 1 is a plurality of garment documenting webpages 1070 hosted by, or accessible by or through, the system 1000, among which webpages 1070 the photographic/videographic documentation of the garment wearers 102 wearing the purchasable garments is posted and made remotely accessible to the garment shoppers 101 for viewing of such content. Such photographic/videographic content is accompanied on each such garment-related page 1070 by displayed garment data uniquely corresponding to each purchasable garment worn in the photographic/videographic content, typically including at least a unique garment identifier (e.g. garment name and SKU or other unique numeric/alphanumeric identifier), the size of the garment as worn in the photographic/videographic content, brand of the garment, price of the garment, material makeup of the garment (e.g. fabric type/composition), elasticity identifier indicative of a stretchable or non-stretchable character of the garment, and the garment's origin of manufacturing (typically identified as country of origin). Other optional content may also include user reviews of the garment, the seller's return policy, and/or other item/seller information helpful in an online shopping context.

Among the webpages 1070 having such content, may be garment-specific webpages each dedicated to a particular purchasable garment, brand-specific webpages dedicated to a particular garment brand and showcasing purchasable garments available from that brand, and/or wearer-specific webpages each dedicated to a particular wearer and showcasing thereon purchasable garments worn by said wearer in posted photographic/videographic content found on, or linked from, that webpage. This way, garment shoppers 101 can shop by browsing/searching for garment types, garment brands, and/or known fashion influencers or other known personalities whose fashion choices or brand sponsorships are appealing or reputable to that shopper.

Also as illustrated in FIG. 1, the system 1000 may also include or be in communication with a publicly available communications network 1080, which may be the Internet or other similar network. As shown, when a disclosed system 1000 is in communication with such a public communications network 1080, some or all of the system components, such as the garment shopper devices 1010, garment wearer devices 1020 and retailer/manufacturer webpages 1070, may communicate via the public network 1080. In other embodiments, the system may use only a public network, such as the Internet, for implementing the disclosed principles, or may include more than two communications networks interspersed between or among components of the system. No limitation to any particular number or type of communications networks or any particular number or type of components for implementing a system and service as disclosed herein is intended or should be inferred.

A body scan software application on each garment shopper's device 1010 is used by each shopper to capture a 3D body scan of the user's body, which may be captured directly by the device using on on-board camera thereof, or alternatively may be captured using a separate camera or body scanner 1100, for example in the case where the garment shopper's device 1010 is a desktop computer lacking a built-in camera. Downloading of the body scan software application, if not already installed on the garment shopper's device 1010, may be initiated from a clickable download link, or scannable quick response code (QR code) on one of the garment-related webpages 1070, or a homepage of the system, being browsed by a new garment shopper 101 not yet registered on the system, or an existing garment shopper 101 already registered with the system, but who has yet to upload a body scan. The resultant body scan data from the captured 3D body scan is forwarded from the shopper's device 1010 to the server 1040 for storage in the database 1050 as part of a respective shopper profile that also contains other shopper-specific data, including at least a unique user ID (e.g. email address, phone number, or username). In the first instance of such capture and logging of a shopper's body scan, such user ID and an associated password are concurrently collected from the shopper and logged by the server in accompaniment to the initial body scan data as part of a shopper registration process. Such initial shopper registration can trigger automated login to the system server, or trigger invitation of the new shopper to login using the newly registered user ID and password. While an initial body scan is typically expected to occur concurrently with, or during, a new shopper registration process, the initial body scan may optionally be deferred to a later time, for example permitting an already registered shopper to defer such body scan until such time as the shopper finds a first garment that they are interested in potentially purchasing, but wishes to first pre-evaluate the potential fit of such garment.

Similarly, downloading of the body scan software application to the garment wearer's device 1020 of any new garment wearer 102 looking to register with the system may be initiated from a clickable download link, or scannable quick response code (QR code) on one of the garment-related webpages 1070, or a homepage of the system, being browsed by a new garment wearer not yet registered on the system, and used in matching fashion to capture an initial 3D body scan in association with a similar user registration process that generates and stores a wearer profile in the database, that likewise stores the body scan data of the wearer's 3D body scan in association with their unique user ID. It will be appreciated that any particular action or function described herein as being performed or undertaken by the garment wearer 102 or garment wearer's device 1020, other than the garment's wearer's participation in capture of the photographic/videographic content of that user in one or more of the purchasable garments, may be performed or undertaken by an agent acting on behalf of the garment wearer and/or a device of that agent's belonging. For example, where the garment wearer 102 is an established influencer and relies on one or more other persons to undertake tasks on their behalf, the agent may be such person(s), whether such person(s) be under the employ of the influencer, their management, their brand sponsor, or an operating entity of the system. Accordingly, the garment wearer's device 1020 is meant to denote one or more devices by which data concerning the garment wearer 102 and the garments worn thereby in the photographic/videographic content, including the recorded photo/video data and 3D body scan data of the garment wearer's body scan(s), is captured for concurrent or eventual logging in the database 1050 for purposeful use by the server 1040 to perform any or all of the various steps and processes described herein that require or benefit from such captured data. While an initial body scan is typically expected to occur concurrently with, or during, a new user registration process, the initial body scan may optionally be deferred to a later time, for example permitting a registered garment wearer 102 to defer such body scan until such time as photographic or videographic content of the wearer 102 wearing a particular one or more garments is uploaded to the system for posting on a garment-related webpage 1070, or is uploaded to an externally hosted garment-related webpage 1070 linked to the system.

Once a garment wearer 102 has uploaded a 3D body scan, their wearer profile in the database will typically be active for body-matching purposes, making it searchable by a body comparison/matching algorithm executed by the server 1040 for the purposes of matching up shoppers 101 and wearers 102 of similar body size and shape, which comparison/matching algorithm executes a computer-automated body similarity analysis comparing the stored 3D body scan of any given shopper 101 against the stored body scans of the collective plurality of any garment wearers 102 having such stored body scans. The analysis identifies a best-matched one or more of analyzed wearer body scans that were found to be of greater similarity to the body scan of the garment shopper 101 than a remainder of said analyzed wearer body scans.

This comparison/matching process may be executed at various points in the timeline or workflow of the shopper experience with the system, and depending on when that timeline/workflow the comparison/matching process is performed, the resultant action may vary. In some instances, one resultant action taken by the server 1040 may be notification to the garment shopper's device 1010 of the identity of the best matched garment wearer(s) 102, which notification may for example contain one or more executable links to one or more of the garment-related webpages 1070 where the photographic and/or videographic content of that garment wearer 102 can be viewed so that the garment shopper 101 can browse such content to identify garments worn by best-matched wearers 102 that may be of interest to the shopper 101 as potential purchases. This type of resultant action, enabling or triggering direction of the garment shopper to relevant content of the best matched wearer(s), may be particularly beneficial to an implementation where one instance of the comparison/matching process is triggered by upload of a shopper's initial body scan, or later upload of an updated body scan after some passage of time, in order to make recommendations to the shopper 101 on which wearers 102 are worth searching/browsing on the system based on the latest body scan data of that shopper 101. Another useful application for the results of the comparison/matching process is to dynamically tailor the content of garment-specific webpages 1070 according to the particular shopper 101 that is browsing such webpages by dynamically compiling the content of such garment-specific webpages 1070, when visited by the particular shopper, with photographic/videographic content specifically of the best-matched wearer(s) 102 that were matched to that particular shopper by the comparison/matching process.

A particularly significant and novel aspect of the invention is that the 3D body scans of the shoppers 101 and wearers 102 are not solely used for matching of shoppers and wearer's by body similarity, but are also used in a novel manner to providing visual feedback to the shopper 101 on just how similar the scanned body of the shopper 101 is to the scanned body/bodies of the best-matched wearer(s) 102, whereby the shopper's estimation of just how well the chosen garment might fit is not solely based on the "best matched" designation of the closest wearer bodies scanned in the database, which alone cannot guarantee an accurate fit assessment of a garment for the shopper's body, given that no two bodies of two different users will ever be a perfect 100% match, and that there will always be some degree of variation in body size and shape between any two users.

To enable the novel visualization of the body similarity/dissimilarity between a shopper's scanned body and a best-matched wearer's scanned body, the sever 1040 executes a comparative body visualization algorithm to which the respective 3D body scans of the shopper and best-matched wearer are inputted, the typical digital form of which is 3D mesh model. The two separate shopper and wearer 3D body meshes are overlaid with one another and combined together in this overlaid relationship into a comparative 3D body model that stores the overlaid meshes in a manner enabling overlaid display thereof on screen with visual distinction between the two overlaid meshes, for example by displaying the two meshes in visually contrasting colours to one another. Such application of contrasting colours may be included throughout the entireties of the two meshes, or be selectively applied at particular areas of the meshes that the server, via execution of a body variance assessment algorithm, has identified as an area of the body at which a difference between two respective measurements taken of the two meshes for a same type of body measurement exceeds a variance threshold. In the latter case, the displayed comparative 3D body model will highlight to the shopper a particular one or more areas of the overlaid 3D body meshes where there is noteworthy dimensional variation between the two meshes.

In some embodiments, multiple variance thresholds may be defined, each associated with a different display/highlight colour or colour tone. As purely a demonstrative, and non-limiting, example, a three-stage threshold scheme could use a three-colour variance visualization scheme, where green might denote a measurement differential that exceeds a lowest variance threshold, yellow might denote a measurement differential that exceeds a middle variance threshold, and red might denote a measurement differential that exceeds a maximum variance threshold. This way, a shopper can interpret any red-toned region of the overlaid meshes as a maximally concerning area of garment fit, any green-toned region of the overlaid meshes as a minimally concerning area of garment fit, and any yellow-toned region of the overlaid meshes as an intermediately concerning area of garment fit, while any areas of the overlaid meshes shown generically in any colour other than these variance-signifying colours denote areas of anticipated good fit based on digitally measured body similarity below the minimal variance threshold, denoting a substantially true match of body measure at such areas, where there would be no concern over garment fit in the case where the shopper is happy with how the garment fits the corresponding area of the wearer's body in the photographic/videographic content showing adornment of the garment by the wearer.

Standardized body measurements used for such variance determination, and optional variance colourization/visualization purposes, and also useable in the aforementioned body comparison/matching algorithm, may include any or all of: fully body height, crotch height (inseam), neck circumference, shoulder width, chest circumference, waist circumference, hip circumference, quad (thigh) circumference, knee circumference, calf circumference, bicep circumference, etc. The threshold-exceeding differential measurements calculated by the body variance assessment algorithm may be visually displayed to the shopper in accompaniment to the overlaid meshes of the comparative 3D body model visualizer, for example by visually tagging a numerical readout of these calculated differential measurements to a corresponding body region of the overlaid meshes of the 3D body model visualizer shown on screen to the shopper.

The creation and visualization display of the comparative 3D body model may be performed at various points in the timeline or workflow of the shopper experience with the system, and depending on when that timeline/workflow the comparison/matching process is performed, the resultant action may vary. For example, the comparative 3D body model for any given shopper 101 may be automatically created once the comparison/matching algorithm has identified one or more best-matched wearers 102 for that shopper, in which case the comparative 3D body model visualizer may be displayed to the shopper 101 on any garment-related page 1070 they visit that contains photographic/videographic content of the based-matched wearer(s) 102 from which such comparative 3D body model(s) was/were created. In an alternative implementation, the comparative 3D body model visualizer may instead only be displayed to a shopper 101 after selection thereby of a garment that they are interested in purchasing from one of the garment-related webpages 1070, for example displaying the visualizer as part of an online order placement/checkout process for completing purchase of that garment. This display at the order placement/checkout stage serves as a final last-check of the anticipated fit of the garment, initial judgement of which, before such final check, may have been based solely on the viewing of the videographic/photographic content of the best-matched wearer(s) 102 already identified as a comparable body reference for the shopper 101. Regardless of where and when this visualization of the overlaid body scans is displayed to the shopper 101, it denotes an opportunity for the shopper 101 to reconsider whether they should order the garment in the same size in which the garment was modeled by the wearer 102 in the viewed videographic/photographic content, or consider ordering in a larger or smaller size given the displayed visualization of the overlaid body meshes and the visually discernable (and optionally colour-coded and/or numerically tagged) variances between the two body meshes.

The comparative body visualization and preferably tagged measurement variance data enables optimal assessment of garment fit/size determination for new and/or used garments purchasable by the garment shoppers 101. The same functionality and gained benefit can also be exploited in a garment rental platform, where the garments are temporarily loaned/rented to the garment shoppers 101 in exchange for financial compensation, whether as a one-off rental transaction, or an ongoing subscription service. Accordingly, the term purchase is not specifically used to necessarily denote a transaction involving transfer of ownership (acquisition), and may refer to temporary rental of a garment for later return, where it is such loan of the garment that is purchased (paid for), and not outright ownership of the garment.

If the best-matched wearer's body scan is a very close match to the shopper's body scan, then the garments that can be seen to fit the wearer's body well in the posted videographic/photographic content can be safely and accurately anticipated to fit the shopper's body equally, or at least comparably, as well. In such instances, the shopper 101 can order the same garment size as shown in the videographic/photographic content posted of the wearer 102 because they are both very close in body shape and size. The preferably displayed threshold-exceeding differential measurements of compared body parts of the overlaid body scan meshes supplements the qualitative visual fit assessment derivable from the displayed visualizer with further quantitative feedback on particular body areas that may be too tight or loose fitting in comparison to the photographically/videographically documented fit on the wearer's body. If the shopper's scanned body is equal to or slightly smaller in size than the body parts of the wearer 102 at the variance flagged areas of the overlaid body meshes, then the garment will predictably fit the shopper's body in matching or slightly looser fashion to how it wears on the wearer's body.

This differential measurement (tight/loose) fit criteria is also affected by the varying tensile properties of different types of garment fabric/material. A garment that is highly elastic allows for varying and notable amounts of stretch, while fabrics such as leather or 100% denim cotton, for example, permit little or no stretch. For this reason, the material makeup of each purchasable garment, and ideally an extra indicator of the elasticity thereof, are included among the garment data display on the garment related pages 1070, so that the shopper can take this into account when making a decision as to whether to size up or size down the selected garment from the size modeled by the wearer based not only on the visualizer and any flagged threshold exceeding variations in body measurement, but also dependent on the stretchable or unstretchable character of the garment in question. Through inclusion of such information in the garment data stored in the database 1050 and displayed on the garment-related webpages 1070, the system further enables informed decision making on appropriate size selection for a garment purchase by the shopper 101, using a combination of the videographic/photographic documentation of the garment worn by a body-matched reference wearer 102, qualitative visualizer of the body similarity between the shopper 101 and that body-matched reference wearer 102, quantitative variance tagging of concerning areas of notable body differentiation therebetween, and indication of elastic or inelastic character of the garment that may or may not accommodate such interbody variation.

Similarly useful information can be communicated to shoppers 101, for similar consideration in the final purchase decision and size selection, within the videographic content posted of the best-matched wearer 102. In such video, the wearer 102 can showcase and discuss the garment in particular detail, including identification of the brand, material makeup, elasticity and/or other material properties, price, return policy, etc., in addition or alternative to text-based inclusion of such information on the same webpage 1070 containing such video content. The garment shopper(s) 101 body-matched to the wearer 102, by viewing such video content of the wearer 102, become(s) educated with respect to the attributes of the garment, in addition to seeing how it wears on a similar body type. Within the video content, the wearer 102 can grasp/pull/comment on specific areas of a garment to determine if, or how much, garment stretch (if any) may be available to accommodate body measurement variations of the matched shoppers 101 relative to the best-matched body of the wearer 102. While such videographic demonstration of elasticity, or lack thereof, may not denote comparable accuracy to the quantitative variance data derived from the overlaid body mesh analysis, it may nonetheless serve as valuable qualitative input to the shopper's decision-making process.

Figure 5:
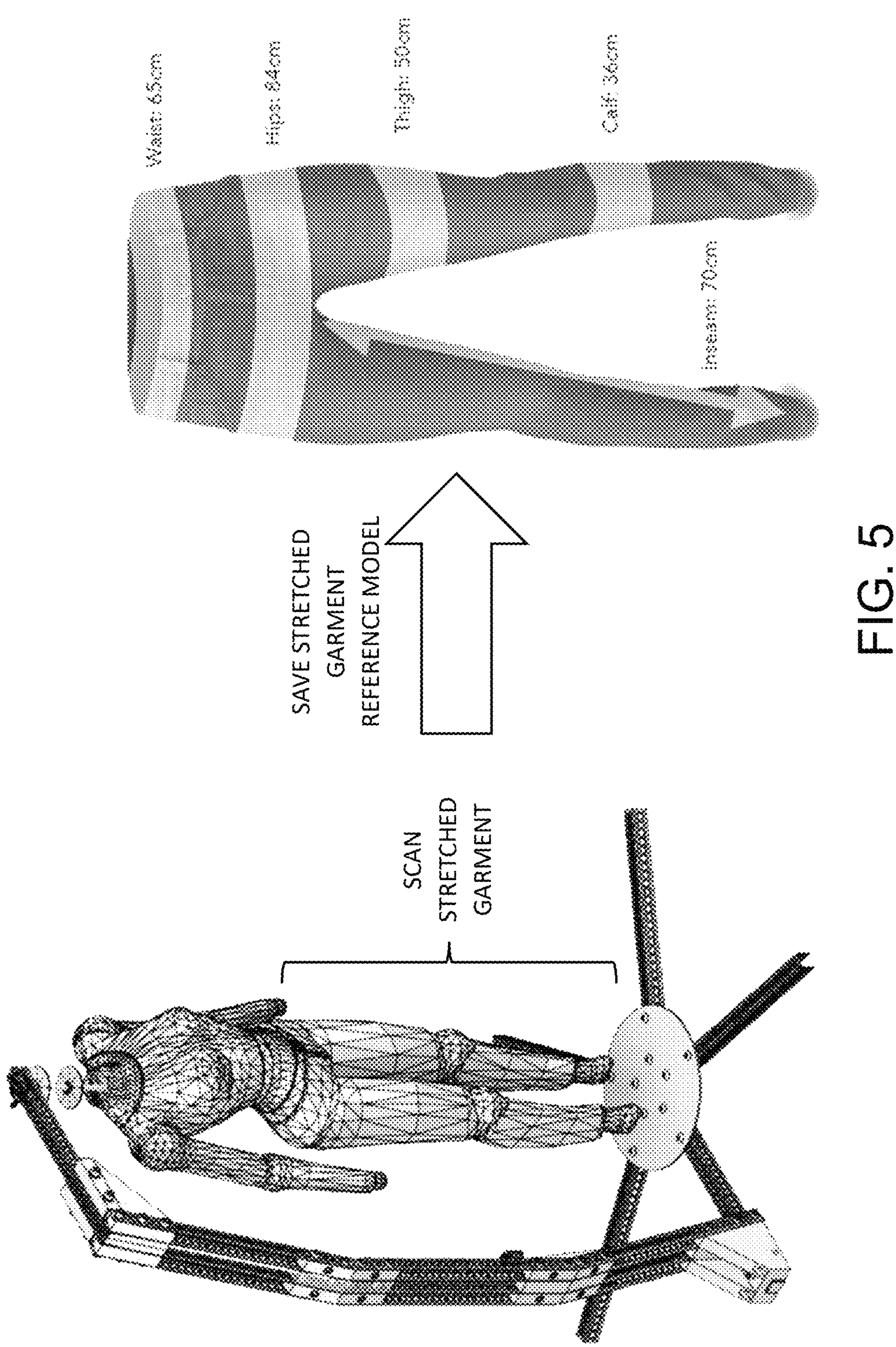
FIG. 5 schematically illustrates 3D scanning of an inflatable 3D body-analogue in an inflated state expanding a garment adorned thereon to a maximally inflated size, for saving of such scan as a reference model of the maximally stretched garment as an additional comparison point for comparatively evaluated fit of the garment on the garment shopper.

The system may also integrate further useful functionality from Applicant's issued U.S. Pat. No. 11,627,772 (the '772 Patent) which shares the same inventor as the present application, and is incorporated herein by reference in its entirety. The '772 patent discloses a robotically and dynamically inflatable mannequin used in combination with 3D scanning of the same type employed herein for 3D body scans of the system users, which in the context of the inflatable mannequin from the '772 Patent can be used to capture a highly accurate 3D model of a garment, adorned on the mannequin, when stretched to the garment's maximally stretched size via controlled inflation of the mannequin up to a failure point of the garment. In the present invention, such scanning is performed of each purchasable garment (in each of its purchasable sizes) in its maximally stretched state on the robotically inflated mannequin, which serves as a human-body analogue of dynamically variable shape and size. A 3D scan is taken of the robotically inflated mannequin in an inflated state thereof corresponding to the maximally stretched state of the garment, which scan may be taken in presence or absence of the garment on the mannequin. This 3D body-analogue scan is stored in the database in association with the SKU or other unique ID of the given garment in the given size, as a reference model denoting a maximally stretched state of that garment of that size. Such scanning of the inflated 3D body-analogue and storage of a reference model of the stretched garment is schematically illustrated in FIG. 5. While illustrated as such, the mannequin or body-analogue need not necessarily be a full-body mannequin or a full-body body-analogue, and could be anatomical analogue for a partial fraction of a human body, and in its simplest form may be embodied in as little as a singular inflatable bladder.

The same visualization algorithm as, or one similar to, that described for overlaying the 3D body scans of the shopper 101 and the best-matched wearer 102 for that shopper 101 may be used to overlay the 3D body-analogue scan with the 3D body scan of the shopper 101, to form a comparative stretch-fit model for visualized display of these overlaid 3D scans in visually distinctive (e.g. again differently coloured) relation to one another to reveal differences between the body of the shopper 101 and the maximally stretched state of the garment at the shopper's currently selected size of that garment. Again, like the comparative body visualization, this stretch-fit visualization may be displayed on the garment-related webpage 1070, or instead only displayed in the order placement/checkout process for purchasing that garment. The 3D body-analogue scan may be overlaid with both the shopper's body scan and the wearer's body scan, in which case the comparative body model and the comparative stretch-fit model may be embodied within a singular model, which may be capable of visualization of any two of the three overlaid meshes at any given time (e.g. at user selection of which visualization subset is desired), or visualization of all three simultaneously. Alternatively, the comparative body model and the comparative stretch-fit model may be visualized in separate visualizers from one another.

The same variant assessment algorithm as, or one similar to, that described above for calculating differential values of body measurements between the shopper's 3D body scan and the wearer's 3D body scan is used by the server 1040 to likewise calculate differential values between body measurements of the 3D body-analogue scan and the shopper's 3D body scan, at least some of which again may be displayed simultaneously with the overlaid meshes of the stretch-fit visualizer. Particularly, calculated differentials indicating that a body measurement of the shopper's body scan exceeds a corresponding body measurement of the analogue-body scan should at least be displayed in tagged reference to the body area at which this problematic differential is identified, since this denotes an inability of the shopper to fit the garment at the shopper's current body dimensions even at the garment's maximally stretched capacity. That said, display of at least some differentials corresponding to an undersized status of the shopper's body relative to the maximally stretched state of the garment (as represented by the analogue-body scan) could also be helpful to communicate to the shopper how much "room" is available before their body would reach the garment's maximally stretched state. The algorithm may be configured to only display differential measurement values at body areas where the shopper's body measurement exceeds the maximally stretched state of the garment, or is within a concerning threshold of proximate, but undersized, relation to that maximally stretched state of the garment, thus denoting the most critical areas of concern that warrant the shopper's attention, as opposed to unfiltered display of all differential measurements, regardless of their criticality, which is a possible alternative, but may be impractical depending on the number of body measurements used for this stretch-fit analysis. Optionally, the results of this stretch-fit analysis could be displayed, without a mesh overlay visualization of the shopper's body scan and the analogue-body scan representative of the garment's maximally stretched state at its currently selected garment size, though the combination of the qualitative stretch-fit visualizer and the quantitative differential measurements (at least at critically identified areas) may be the optimal preference.

In summary, the system and methodology described above delivers highly accurate online shopper assessment tools by which garment size and fit can be qualitatively visualized and/or quantitively informed, in reference to a bodily matched wearer/demonstrator of the garment, prior to the shopper making an informed final size selection and purchase of a garment, whether from an online marketplace built into the system, or from a separate online source (retailer website, brand website, third party marketplace). Using fashion influencers or other known fashion-forward personalities to market various brands of garments on a centralized marketplace built into the system, and/or on retailer websites, and/or on brand websites allows influencers to earn commission revenue driving online traffic to such online shopping sites, to the benefit of all parties involved.

The forgoing description reflects a typical implementation of how various computing tasks may be distributed among the user devices and the server, with the user devices 1010, 1020 being used primarily for capture of body scans, transmission thereof to the server 1040 for processing thereof, and display of the qualitative visualization and quantitative measurements results from the server to the garment shopper 101, where the body comparison/matching algorithm, comparative body visualization algorithm and body variance assessment algorithm are all executed by one or more software applications executed by the server(s) 1040, but it will be appreciated that any one or more of these algorithms, in entirety or in part, may alternatively be executed elsewhere in the system, for example at the shopper devices 1010, provided that any necessary data from the database 1050 or other data resource necessary to the performance of such algorithms is made available and communicated to such other computing resource for such purpose at one or more points of appropriate timing in the executional workflow of the inventive methodologies.

In another application for the comparative 3D body scan visualizer for overlaid display of two captured body scans, the same overlaid visualization can be performed of two or more body scans captured at different points in time of the same user 101 in order to provide visualization of changes in the body shape of that user 101 over time, for example for the purpose of providing accurate visual feedback on a user's progression in weight loss or athletic training (e.g. muscle building) endeavours, a user's advancement through a pregnancy term, or any other applications where visualization of changing body shape over time may be helpful, including monitoring thereof by health care professionals for various purposes, including general health and wellness, age related regression, etc. Likewise, the same calculation of differential body measurements between any two or more such body scans captured at different respective points of time can be calculated in matching fashion to the differential body measurements captured above for comparison of a garment shopper's body against a closest matched body double (fashion influencer or other online-documented wearer of the garment), so that such differential measurements can be displayed to the user in accompaniment of the overlaid body scans of the comparative body visualizer to supplement the visual body change feedback displayed thereby with quantified measure of the body changes visualized therein.

Figure 3:
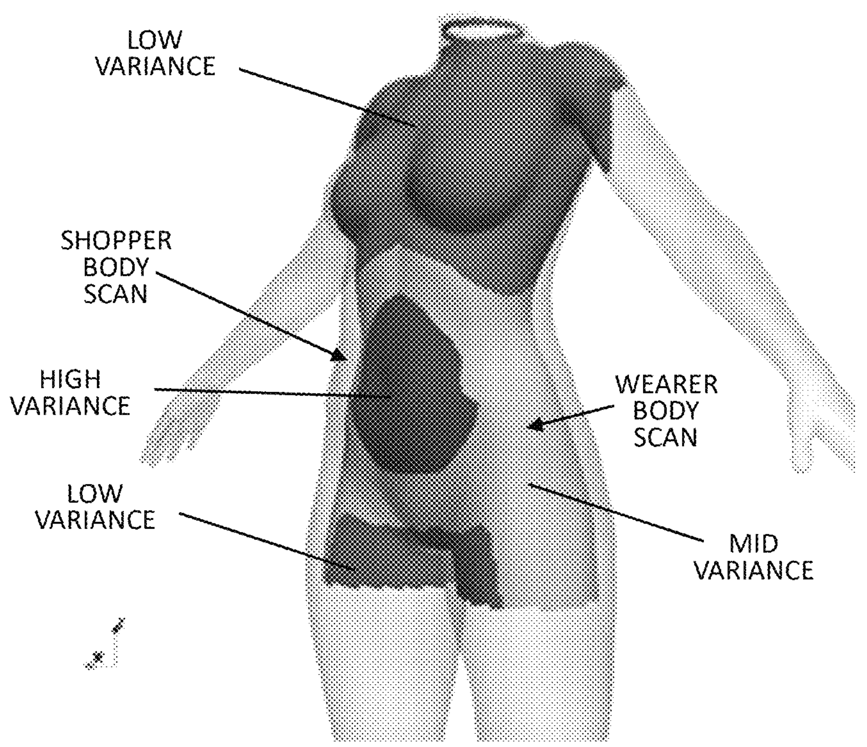
FIG. 3 is a schematic illustration of a body similarity visualizer displayed to an online garment shopper using the system of FIG. 1 for overlaid comparison of their body shape and size against those of a fashion influencer to whom the shopper was matched by body similarity based on 3D body scans of both users, from which the shopper can predictively gauge how well a garment modeled online by that influencer will fit the shopper.
Figure 4:
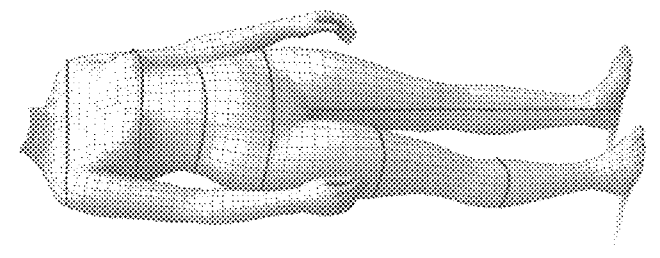
FIG. 4 is a schematic illustration of an alternative implementation of the body similarity visualizer using concurrent side-by-side display of the respective body scans of both users, rather than an overlaid visualization thereof, in accompaniment by absolute and/or differential body measurements of the two body scans for comparative evaluation of garment fit on the bodies of the two users.
Figure 4:
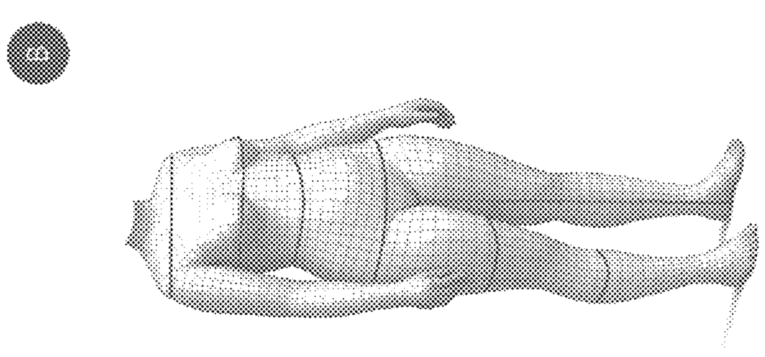

While FIG. 3 denotes one preferred embodiment of the comparative body visualizer that specifically provides overlaid visualization of the garment shopper and garment wearer body scans, alternative implementations of the visualizer may instead employ concurrent individuated visualization of the two body scans in neighbouring side-by-side, or otherwise concurrently visible, relation to one another, as demonstrated in FIG. 4, which also demonstrates optional markup of any visualized body scan with annotation of various anatomical measurements thereof, and accompanying display of the measurement values of those anatomical measurements (columns A & B of the illustrated display chart), and/or the calculated differential values thereof between the two body scans (column A-B of the illustrated display chart).

Figure 6:
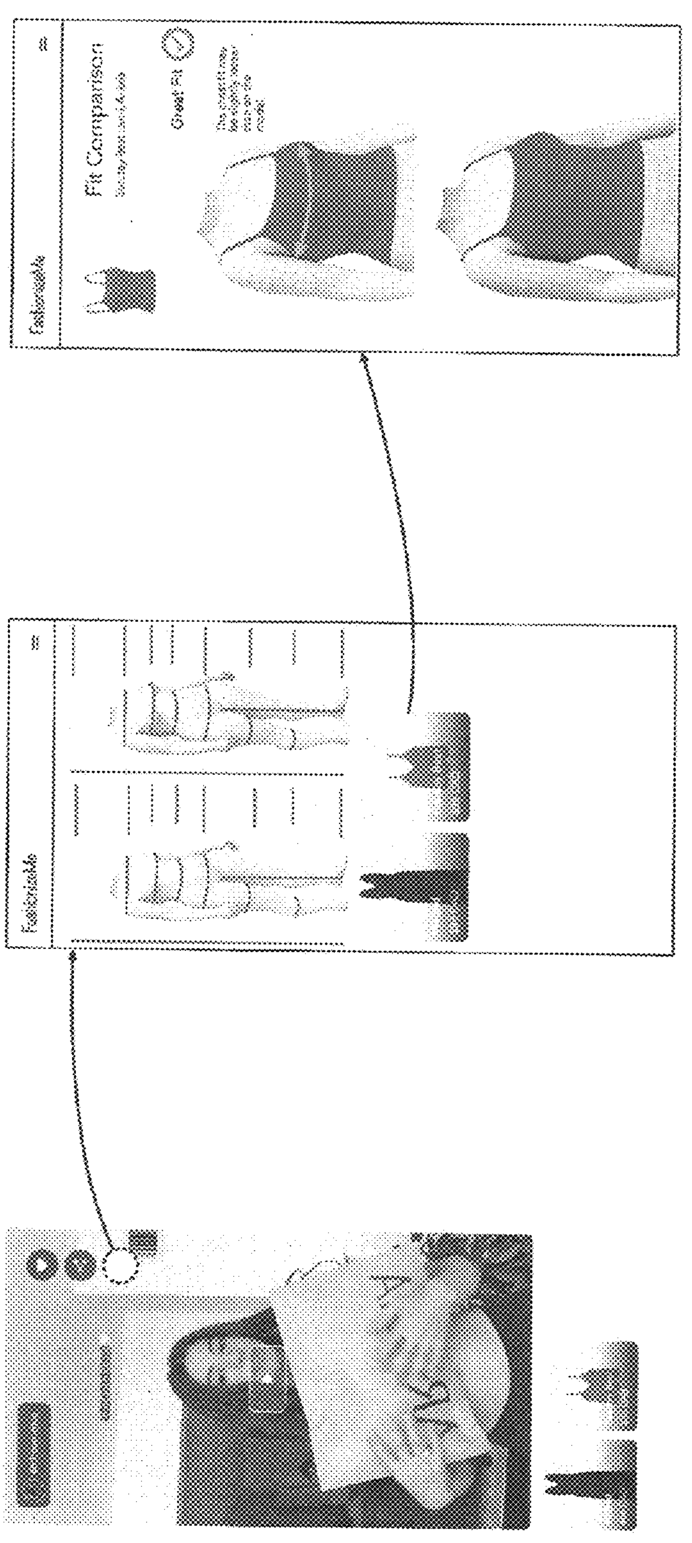
FIG. 6 schematically illustrates a shopper's user experience at different stages of user interaction with the system, in this instance including initial viewing of the influencer's online content followed by a multi-stage comparative visualization process that includes a first comparative visualization of body scans of the shopper and influencer, similar to FIG. 4, and a second comparative visualization of the garment itself when modeled on those respective body scans.

As illustrated in FIG. 6, in which the first (leftmost) panel illustrates viewing of a fashion influencer's online content that includes demonstrative wearing of one or more purchasable garments, the comparative visualization process executed using the respective body scans of the shopper and the fashion influencer may include multiple visualization stages of different visualization type, in this instance starting in the second (middle) panel of the Figure with a body scan visualization similar to FIG. 4 where non-garmented visualizations of the shopper's and influencer's respective body scans are displayed (side by side in this example, but optionally overlaid in other examples) together with numerical or symbolic indicators of various anatomical body measurements of the two body scans (or calculated differentials thereof) for comparative purpose of body size and shape between the influencer and the shopper, independently any particular garment. In the next stage of visualization, shown in the final (rightmost) panel of the figure and optionally triggered by shopper selection from among one or more purchasable garment selections displayed with the body scan visualization, a 3D visualization of the (selected) garment is visually overlaid on each of the two 3D body visualizations for the shopper's visual evaluation of the relative fit of the garment on the shopper and influencer bodies.

One or more indicators of computer evaluated fit quality may be concurrently and adjacently displayed with the shopper-worn visualization of the garment, which one or more indicators may include, or be derived from, all or a subset of the body differential and/or stretch-fit deviation values assessed between the shopper's body scan data, the influencer's body scan data and/or the stretched-garment reference model. The one or more indicators may include a general qualitative fit-assessment score (great, good, acceptable, poor), and optional accompaniment by anatomically specific feedback on one or more areas of noteworthiness, e.g. pointing out areas of greatest differential measure between body scans that indicate discernably more tight or loose fit on the shopper versus the influencer, or areas of concern where the shopper's body scan closely approaches, reaches or exceeds the maximally stretched dimensionality of the garment.

Since various modifications can be made in the invention as herein above described, and many apparently widely different embodiments of same made, it is intended that all matter contained in the accompanying specification shall be interpreted as illustrative only and not in a limiting sense.

The invention claimed is:

1. A computer-implemented method of generating a comparative 3D body model for visual assessment of garment fit assessment by an online garment shopper in an online shopping environment, said method comprising:

by one or more processors, and via execution thereby of computer readable statements and instructions stored in one or more non-transitory computer readable media:

(a) storing in non-transitory computer readable memory a first 3D mesh model of a 3D body scan of a garment wearer, distinct from said online garment shopper, who has been visually documented wearing one or more purchasable garments offered for purchase in said online shopping environment, visual documentation of which is available for online viewing by said online garment shopper using an electronic device connected to a communications network;

(b) receiving a second 3D mesh model of a 3D body scan of said online garment shopper;

(c) from said first and second 3D mesh models of said 3D body scans of the garment wearer and the online garment shopper, creating a comparative digital 3D body model that embodies visually overlaid representations of at least parts of the 3D mesh models of said 3D body scans of the online garment shopper and the garment wearer, in visually distinctive relation to one another to reveal differences in body size and shape between the online garment shopper and the garment wearer, wherein creating the comparative digital 3D body model comprises executing a body variance assessment algorithm to identify one or more areas where a dimensional variation between the first and second 3D mesh models exceeds at least one variance threshold, and wherein the visually distinctive relation comprises displaying the identified one or more areas in one or more highlighting colors that contrast one or more other areas at which the at least one variance threshold is not exceeded; and (d) enabling online viewing of said comparative digital 3D body model by said online garment shopper over said communications network, from which online viewing said online garment shopper can visually gauge a body similarity between said online garment shopper and said garment wearer, which in combination with viewing by the online garment shopper of said visual documentation of the garment wearer and the one or more purchasable garments, enables informed judgement by said online garment shopper as to how well any of said one or more purchasable garments would fit said online garment shopper.

2. The method of claim 1 wherein said body scan of the garment wearer is one of a plurality of 3D body scans of a plurality of garment wearers each embodied as a respective 3D mesh model and each stored in said computer readable memory, and the second 3D mesh model of the garment wearer whose visual representation is embodied in the comparative digital 3D body model made accessible to the online garment shopper in step (d) is selected, prior to step (d), from among the respective 3D mesh models of said plurality of 3D body scans based, at least in part, on a computer-automated body similarity analysis comparing the second 3D mesh model of the online garment shopper against said respective 3D mesh models of said plurality of 3D body scans, from which said computer-automated body similarity analysis identifies a best-matched one or more of the respective 3D mesh models of the plurality of 3D body scans of greater similarity to the second 3D mesh model of the online garment shopper than a remainder of said respective 3D mesh models of the plurality of 3D body scans.

3. The method of claim 1 comprising, based on the 3D mesh models of the body scans of the online garment shopper and the garment wearer, calculation of one or more body differential values each corresponding to a measurement difference, in a respective body measurement, between the second 3D mesh model of the online garment shopper and the first 3D mesh model of the garment wearer.

4. The method of claim 3 comprising, in step (d), enabling viewable display of at least one of said one or more body differential values to the online garment shopper in a same user interface in which viewing access to said comparative digital 3D body model is provided, thereby providing quantifiable measure of a potential relative garment looseness or tightness at one or more body parts where said respective body measurement differs between the second 3D mesh model of the online garment shopper and the first 3D mesh model of the garment wearer.

5. The method of claim 1 wherein step (a) also comprises storing, in said computer readable memory and for at least one of said purchasable garments, a third 3D mesh model of a 3D body-analogue scan of a variably inflatable human body analogue at an inflated size thereof corresponding to a maximally stretched state of said one of said purchasable garments.

6. The method of claim 5 comprising creating a comparative stretch-fit digital 3D body model that embodies overlaid visual representations of the second and third 3D mesh models, in visually distinctive relation to one another to reveal differences between the body size and shape of the online garment shopper and the maximally stretched state of said one of said purchasable garments.

7. The method of claim 5 comprising, based on the third 3D mesh model of the inflatable human body analogue and the second 3D mesh model of the online garment shopper, calculation of one or more body stretch-fit deviation values each corresponding to a difference between a body measurement, at a respective body part, of the second 3D mesh model of the online garment shopper and a garment measurement at a corresponding part of said one of the garments in the maximally stretched-state thereof.

8. The method of claim 7 comprising enabling viewable display of at least one of said one or more body-garment stretch-fit deviation values to the online garment shopper in a same user interface in which viewing access to said comparative stretch-fit digital 3D body model is provided, thereby providing quantifiable measure of a garment looseness or tightness at one or more body parts where said body measurement differs from the stretched garment measurement.

9. The method of claim 5 wherein the visually overlaid representations in the comparative digital 3D body model further comprise a visual representation of the third 3D mesh model of the inflatable human body analogue, in visually distinctive relation to the visual representation of the second 3D mesh model of the online garment shopper to reveal differences between the body size and shape of the online garment shopper and the maximally stretched state of said one of the garments.

10. The method of claim 9 comprising, based on the third 3D mesh model of the inflatable human body analogue and the second 3d mesh model of the online garment shopper, calculation of one or more body-garment stretch-fit deviation values each corresponding to a difference between a body measurement, at a respective body part, of the second 3D mesh model of the online garment shopper and a stretched garment measurement at a corresponding part of said one of the garments in the maximally stretched-state thereof.

11. The method of claim 1 wherein step (d) comprises displaying said comparative digital 3D body model on a website on which at least a subset of said one or more purchasable garments is advertised and purchasable.

12. The method of claim 1 further comprising, by said one or more processors, receiving a purchase request from the online garment shopper for at least one of said one or more purchasable garments, and creating a customer order for fulfillment of said purchase request.

13. The method of claim 12 further comprising, by said one or more processors, generating a shipping label for shipping of said at least one of said one or more purchasable garments to the online garment shopper.

14. The method of claim 12 comprising shipping said at least one of said one or more purchasable garments, directly or indirectly, to said online garment shopper.

15. One or more non-transitory computer readable media in which there are stored computer readable statements and instructions executable by one or more processors so as to, when executed, perform at least step (a) through (d) of claim 1.

16. The method of claim 1, wherein the at least one variance threshold comprises a plurality of distinct variance thresholds, and wherein the one or more highlighting colors comprises a plurality of distinct highlighting colors or color tones, and each distinct highlighting color or color tone corresponds to one of the plurality of distinct variance thresholds.

17. The method of claim 16 wherein the plurality of distinct variance thresholds comprise three variance thresholds, and the plurality of distinct highlighting colors comprises three colors or color tones.

18. A computer-implemented method of generating a comparative 3D body model for visual assessment of garment fit by an online garment shopper in an online shopping environment, said method comprising:

by one or more processors, and via execution thereby of computer readable statements and instructions stored in one or more non-transitory computer readable media:

(a) storing in non-transitory computer readable memory a first 3D mesh model of a 3D body scan of a garment wearer, distinct from said online garment shopper, who has been visually documented wearing one or more purchasable garments offered for purchase in said online shopping environment, visual documentation of which is available for online viewing by said online garment shopper using an electronic device connected to a communications network;

(b) receiving a second 3D mesh model of a 3D body scan of said online garment shopper;

(c) executing a body variance assessment algorithm on the first and second 3D mesh models to identify one or more areas where a dimensional variation between the first and second 3D mesh models exceeds at least one variance threshold; and (d) generating, and enabling online viewing of, a digital 3D body model derived from at least one of the first and second 3D mesh models, wherein the identified one or more areas are displayed on said digital 3D body model in one or more highlighting colors that contrast with one or more other areas at which the at least one variance threshold is not exceeded, thereby enabling the online garment shopper to visually gauge a body similarity between said online garment shopper and said garment wearer.

19. The method of claim 18, wherein the at least one variance threshold comprises a plurality of distinct variance thresholds, and wherein the one or more highlighting colors comprises a plurality of distinct highlighting colors or color tones, and each distinct highlighting color or color tone corresponds to one of the plurality of distinct variance thresholds.

20. The method of claim 19 wherein the plurality of distinct variance thresholds comprise three variance thresholds, and the plurality of distinct highlighting colors comprises three colors or color tones.

* * * * *